United States Patent [19]

List et al.

[11] 4,211,506
[45] Jul. 8, 1980

[54] METHOD AND APPARATUS FOR THE METERED CONVEYING OF PULVERULENT SOLIDS

[75] Inventors: Ferdinand List, Marl; Julius Klos, Recklinghausen; Helmut Alfs, Marl, all of Fed. Rep. of Germany

[73] Assignee: Chemische Werke Hüls Aktiengesellschaft, Marl, Fed. Rep. of Germany

[21] Appl. No.: 893,460

[22] Filed: Apr. 4, 1978

[30] Foreign Application Priority Data

Apr. 23, 1977 [DE] Fed. Rep. of Germany ....... 2717920

[51] Int. Cl.² .............................................. B65G 53/48
[52] U.S. Cl. ................................................... 406/55
[58] Field of Search ................. 302/50; 222/195, 240, 222/241; 366/81, 102, 156, 157, 158, 295; 418/48; 425/207, 208; 406/55, 61

[56] References Cited

U.S. PATENT DOCUMENTS

| | | | |
|---|---|---|---|
| 873,559 | 12/1907 | Koontz | 425/207 |
| 3,004,799 | 10/1961 | Tikal | 302/50 |
| 3,271,081 | 9/1966 | Huddleston | 418/48 |
| 3,380,391 | 4/1968 | John | 418/48 |
| 3,693,842 | 9/1972 | Cozzarin et al. | 302/50 |
| 3,768,171 | 10/1973 | Bird et al. | 34/12 |

FOREIGN PATENT DOCUMENTS 560826  4/1975  Switzerland ............................ 222/241

Primary Examiner—Jeffrey V. Nase
Attorney, Agent, or Firm—Gilbert L. Wells

[57] ABSTRACT

Method and apparatus for the metered conveying of pulverulent solids with the aid of an eccentric screw pump. The pulverulent solids such as terephthalic acid (TPA) are mechanically or pneumatically loosened in the receiving chamber of the pump.

1 Claim, 2 Drawing Figures

METHOD AND APPARATUS FOR THE METERED CONVEYING OF PULVERULENT SOLIDS

CROSS REFERENCE TO RELATED APPLICATIONS

Applicants claim priority under 35 USC 119 for application P 27 17 920.0 filed Apr. 23, 1977 in the Federal Republic of Germany.

The disclosure of copending application Ser. No. 704,955 of Ferdinand List et al filed July 13, 1976 now U.S. Pat. No. 4,162,365 and corresponding to British Pat. No. 1,237,786 is incorporated herein to show the state of the art of liquid phase air oxidation processes for making phthalic acids and the crude terephthalic acid containing terephthaldehydic acid starting materials used in the present invention.

BACKGROUND OF THE INVENTION

The field of the present invention is conveying and metering pulverulent, dry solids and the present invention is particularly concerned with chemical processes in which the solid should be metered into an apparatus in which there is a superatmospheric pressure of a gaseous system. At the same time, a sure sealing against the surge chamber is needed in this case. But the task is made especially difficult when the gas chamber under superatmospheric pressure has an elevated temperature and contains the vapor of a liquid, which vapor would cool off in the conveyed powder upon flashing back and would condense in the powder.

For example, such a problem exists when terephthalic acid (TPA) and methanol (M), which are solid and liquid, respectively, at normal conditions, are to be esterified to terephthalic acid dimethyl ester (DMT) at an elevated temperature in the gas phase. The state of the art of methods and apparatus for the esterification of TPA and M to DMT may be ascertained by reference to British Pat. No. 1,305,290 and U.S. Pat. Nos. 3,617,226; 3,886,200; 3,940,431; 3,972,912; 3,980,431 and 4,015,943, the disclosures of which are incorporated herein. During these processes, as disclosed in the British and U.S. Patents, pulverulent TPA along with M are fed into a rotary furnace, fluidization oven or preliminary reactor, which are at an elevated temperature and under increased pressure, and the reactants are esterified, partly directly, partly in devices connected at the outlet side, wherein the gaseous reaction material can also partly be circulated. In any case, pulverulent, dry TPA is metered into an apparatus containing a hot gas mixture made from TPA, M, DMT, terephthalic acid monomethyl ester and water. The apparatus of U.S. Pat. Nos. 3,980,441 and 4,015,943 are especially advantageous; since M is used here only in a slight excess, but at the same time the work is conducted at 300° to 340° C. at a guage pressure of 1 bar, the uniform and reliable conveying and metering of the TPA becomes especially important.

In the prior art dry, pulverulent material is metered into an apparatus containing a hot gas mixture by conveying a suspension of TPA in M, e.g. with the aid of a centrifugal pump. Instead of vaporizing the M and bringing it up to the required reaction temperature before its entry into the apparatus, the heat is applied by heat exchange surfaces which are arranged inside of the reaction system and during this process, these surfaces quickly become encrusted with TPA which is hard and lumpy even though constantly being scraped off by rotating scrapers and it eludes the desired reaction.

The prior art pneumatic conveyance is also elaborate and unsatisfactory, as the solid and the conveying gas must be in a determined mass ratio, as the entire system must be heated because of the M, and as a corresponding inlet pressure of the conveying gas must be maintained. Therefore, a metered feeding device for the TPA against the pressure system is necessary, e.g. a screw or a bucket wheel under a pressure provided in the heated TPA container, wherein the gas seal can be attained with the aid of bucket wheel charging units or double flap valves with pressure equalization. In all of these devices in which TPA is periodically fed in and discharged, it is unavoidable that vaporous M penetrates backwards and causes disturbances of all sorts. But particularly the exact continuous adjustment of a mass flow of pulverulent solid is not the concern, but rather the discontinuous periodical metered feeding of small quantities.

Thus the essential prerequisite of many commercial processes which require the constant conveying and metering of a powder remains unfulfilled. In the selected example, the only way to attain that the TPA is vaporized free from residue and completely esterified in dependence on the residence times, the concentration ratios and the temperature profiles based on the mass ratios, is by the continuous metered feeding of both reactants, so that the given arrangement is made maximal use of and the reaction mixture obtained can be simply and constantly worked up.

SUMMARY OF THE INVENTION

Having in mind the limitations of the prior art, it is an object of the present invention to provide a method and apparatus for metering a dry, pulverulent material into an apparatus containing a hot gas mixture.

This object is achieved, according to the present invention, with the aid of an eccentric screw pump (ES-pump) where the pulverulent solids are pneumatically or mechanically loosened in the receiving chamber of the pump.

The solution of the present invention cannot be derived from the respective technical literature, rather it contradicts that information. Thus J. Leuschner writes in "Kleines Pumpenhandbuch fuer Chemie und Technik," (Little Pump Handbook for Chemistry and Engineering) Verlag Chemie Publishers (1967), p. 234, that pulverulent dry substances can be conveyed under suitable conditions insofar as they still exhibit a certain residual moisture for the purpose of lubrication; dry operation must be avoided under all circumstances. According to Fuchslocher/Schulz, "Die Pumpen" (Pumps), Springer-Verlag Publishers (1959), p. 214, besides highly fluid, also viscous media as well as liquids with arenaceous or other fine-granular or fibrous additions are suitable as conveying means; Chem.-Ing.-Tech. 37, 45 (1965) says that same thing. "Ullmanns Encyklopaedie der technischen Chemie" (Ullmann's Encyclopedia of Technical Chemistry) also names in volume 1, (1951), p. 84, substances having up to 10% solids as well as slurries, in volume 3, p. 170, highly fluid and very viscous, barely still fluid media. Thus, correspondingly it follows from "Pumps-Pompes-Pumpen" 16, pp. 380 to 385 (1967), that solids-liquid mixtures are also able to be conveyed, among them media having a large solids content, wherein the ES-pumps must not in any case operate dry, because the frictional heat, which cannot be eliminated, burns the contact surface of the stators; therefore, a dry operation safeguard is recommended, e.g. in the form of an external water supplying device.

From this state of the art, a unanimous prejudice is to be derived against the claimed conveying of solids in ES-pumps.

Considered an ES pump would be a rotating displacement pump whose rotor of helical configuration having a circular cross section works in a stator usually made from an elastomer, which stator is also of helical configuration but has an elongated cross section and a doubled pitch, so that axially shifting, sealed off cavities are formed which are defined by a sealing line and which cause a continuous conveying stream.

BRIEF DESCRIPTION OF THE DRAWINGS

The invention may best be described by reference to the drawings, wherein.

DESCRIPTION OF THE PREFERRED EMBODIMENTS

Figure 1:
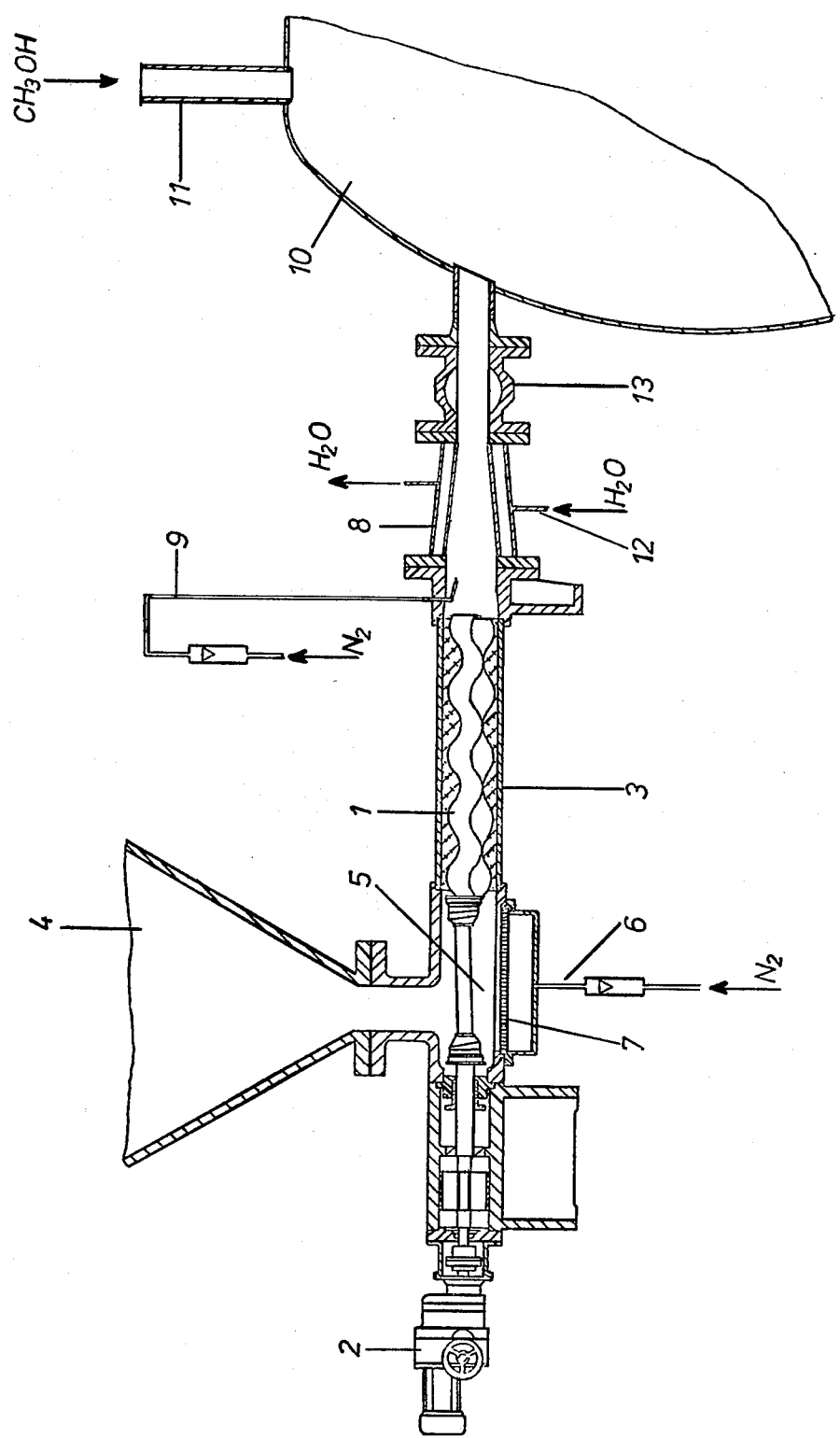
FIG. 1 is a diagrammatic representation of an embodiment of the ES-pump apparatus of the present invention.

With particular reference to FIG. 1, the ES-pump is shown having rotor 1 made from high-grade steel which is driven by an electric motor having an infinitely variable speed control 2, and a stator 3 made from an elastic material such as for example natural rubber, butyl rubber, NEOPRENE, HYPALON, VITON, soft-PVC, etc. The hot TPA entering from the storage container 4 into the receiving chamber 5 of the pump is fluidized with nitrogen to prevent bridge formation and solidifying. For this purpose, a nitrogen stream 6 is introduced by bubbling into the pump chamber 5 by way of the bottom sintered plate 7. The ES-pump is self priming and upon leaving the pump, the TPA conveyed in the direction from the suction side to the pressure side enters the transition section 8, which is flushed with a weak nitrogen stream 9. Thus when the TPA conveyance is interrupted, no 320° to 330° C. hot methanol vapor from the fluidized bed reactor 10 such as shown in FIG. 4 of U.S. Pat. No. 3,980,441 gets into the pump head to damage the elastomer material of the stator, on the one hand, and thus, on the other hand, no TPA deposits appear in the intermediate section 8 during simultaneous moistening of the TPA by condensing methanol. As further protection for the temperature-sensitive stator from the high temperatures in the fluidized bed reactor 10 into which a 320° to 330° C. hot $CH_3OH$ vapor stream is introduced via a feed line 11, the intermediate section 8, located between the pump and the fluidized bed reactors can be cooled with water 12.

Figure 2:
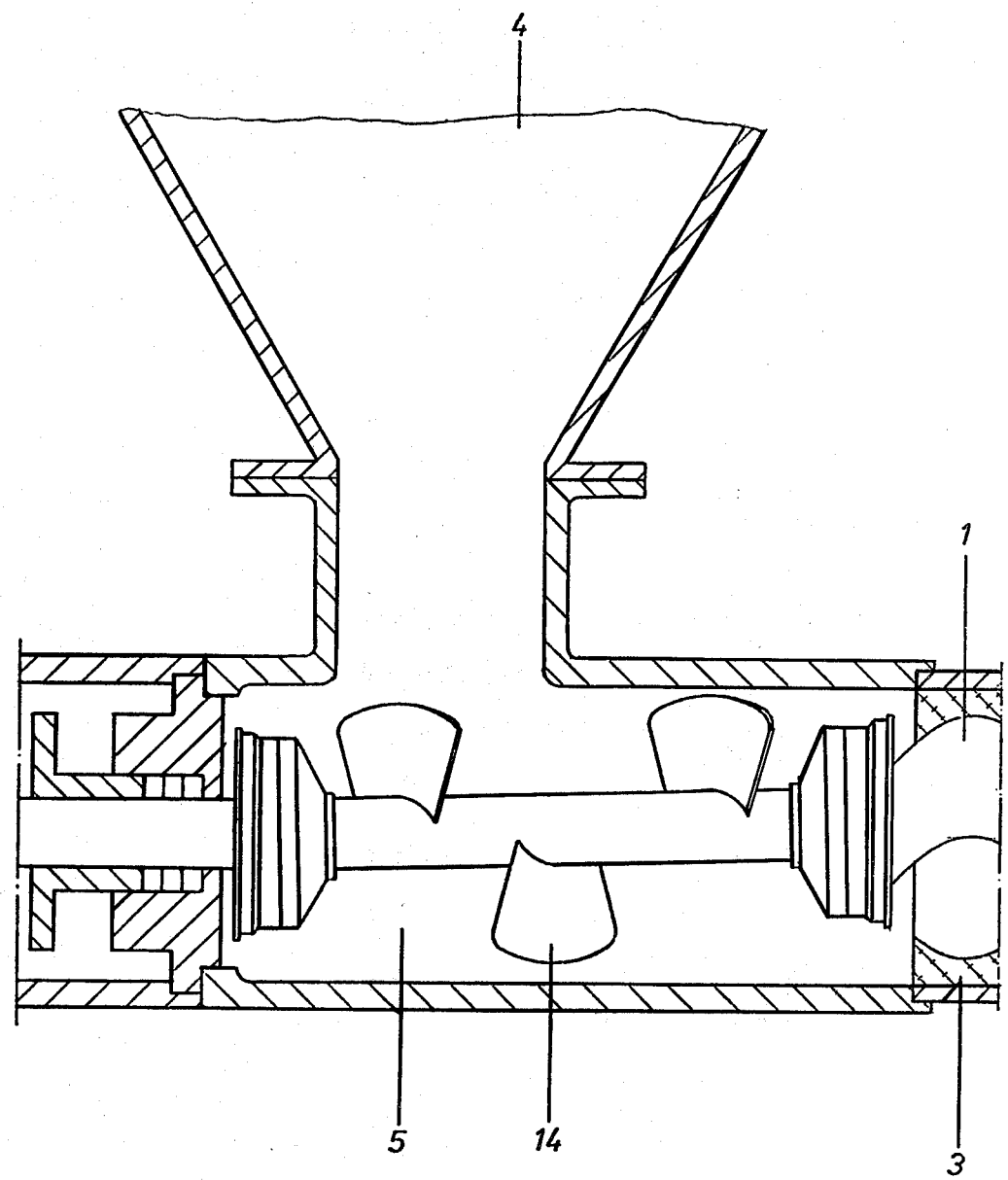
FIG. 2 is a detailed showing, in cross section, of FIG. 1 showing another embodiment.

In the embodiment of FIG. 2, agitator vanes 14 are mounted on the pump shaft for the mechanical loosening.

Considered a pulverulent solid conveyable according to the invention is one that has self-lubricating qualities, such as for example, talc, graphite and carbon black, consequently a substance whose particles do not tend to stick to each other after an application of pressure.

Furthermore, a substance suitable according to the invention is TPA, especially one as obtained when p-xylene is oxidized with the aid of air in the presence of solvents like aliphatic carboxylic acids, acetic aldehyde, methyl ethyl ketone in the presence of heavy-metal ions, and preferably one in whose manufacture p-xylene is oxidized with the aid of air in an acetic acid solution in the presence of heavy-metal ions and bromine ions in accordance with British Pat. No. 1,237,786 and U.S. Patent Application No. 704,955. According to the present invention, the solid is loosened in the receiving chamber of the pump with the aid of a mechanical or pneumatic device.

When a pneumatic loosening is used, any gaseous substance is suitable as the fluid gas that does not corrode the pump material, that behaves inertly with respect to the substance to be conveyed, and that does not disturb the reactions in the optionally adjoining devices into which the solid is conveyed. Thus, frequently work can be conducted with dry air or with nitrogen, in case no dust explosion can occur.

The quantity of gas is measured in such a way that a specific surface loading of from 0.5 to 6, preferably 1 to 5, especially 2 to 4 $m^3$ gas/min. and $m^2$ of loosening area is adjusted with reference to the stream-exposed plate.

The gas flowing in loosens the fine-granular layer of the conveyed material and thus prevents the agglomeration and the bridge formation of the conveyed material in the receiving chamber. The loosened conveyed material continues to flow into the unit satisfactorily, just as a liquid. In general, only minimal amounts of fluidizing gas are respectively also conveyed in the upper portion of the dead space in the chamber. The fluidizing gas transported by way of the dead spaces in the chamber flows out of the pump outlet and there unites with the purging gas, if desired.

The loosening of the conveyed material in the receiving chamber occurs when the forces of the gas flowing in counteract the force of gravity of the bulk. That means the gas pressure depends on the bulk height and the bulk weight of the conveyed material. In the case of terephthalic acid (bulk weight=0.8 kg/l), 0.08 bar per $cm^2$ is necessary at a given bulk height of 1 m.

The gas pressure in the cavities corresponds to the pressure in the pump intake zone. By far the largest portion of the fluidizing gas penetrates the bulk material from below upwards and is passed off above the receiving chamber; only an infinitesimal portion of this gas passes through the pump. It has been found to be expedient that the gas is allowed to escape upwards through the supply funnel set up for the conveyed material.

It is clear from the above that fluidizing, known in itself, is employed to attain the pneumatic loosening: if a gas with an increasing velocity flows through the bulk of a fine-granular solid from its base, the so-called stream-exposed plate, then the loss of pressure of the gas rises over the height of the bulk with an increasing velocity until suddenly the solid bulk loosens upon reaching the so-called loosening point and enters the flow state. In this state (also called fluidized layer, fluidized bed or fluidized solid bed) the layer begins to swell up, to expand, to bubble. Thereby similar phenomena occur as with a boiling liquid, e.g. gas bubbles or also tubular channels break through the layer.

Since merely bridge formation or agglomeration of the solid in the receiving chamber is to be prevented with the introduction of the gas by bubbling it into the conveyed material according to the invention, the entire layer of the fine-granular solid need not be brought to the state of an ideal fluidized layer when very fluid products are used. It is sufficient if this state of loosening or swelling up occurs sporadically at random, i.e. practically ever-changing points of the conveyed material. If desired, the loosening gas can be blown in sectionwise, i.e. this can be conducted with a relatively small amount of gas, wherein a pulsating effect is achieved (pulsating gas supply=quasi homogeneous fluidized layer).

The fluidizing of the solids succeeds in that the gas is introduced by nozzles, for example. In contrast, a stream-exposed plate is preferably used. This plate should offer sufficient resistance to the flowing through of the gas so that the same inlet pressure prevails in the gas chamber below the plate despite a limited number of gas feed points. The gas should also be uniformly dispersed and the flow of particles of solid should be exposed to the smallest possible resistance above the plate.

Consequently, the stream-exposed plate can be embodied in various ways. For instance, it can consist of a flexible material such as natural or synthetic fibers, metal cloth, porous polyethylene, polystyrene, polytrichloroethylene, or polytetrafluoroethylene or of a rigid material such as porous ceramic bricks, synthetic resin plates, sintered powdered metals, or finely punched (e.g. electrolytically punched) high-grade steel plates.

The porosity should be chosen in such a way that none of the conveyed material is able to penetrate into the fine ducts; for the conveyance of TPA, a pore size of approximately 5 to 10μ is suitable.

Instead of the pneumatic loosening, represented in FIG. 1, the fluidizing of the conveyed material can also be achieved according to the invention in that the conveyed material is mechanically agitated in the receiving chamber. This is expediently attained with agitator vanes placed on the shaft, as they are represented as numeral 14 in FIG. 2.

Especially in those cases in which the pulverulent solid is conveyed in an apparatus under pressure, it is advantageous that the pump outlet be flushed with a gas. This is possible, for example, in that a transition section is connected to the pump outlet through which transition section a weak flow of a gas is introduced, expediently the same gas employed for the fluidizing step. Thus upon shutdown of the pump a possibly hot and gaseous reactant condensing in the interior of the pump is prevented from flashing back out of the apparatus.

Furthermore, it can be advantageous to cool the transition section between the pump and the apparatus, for example by a water jacket. Such a cooling acts to prevent a hot, attached apparatus from damaging the heat-sensitive stator or prematurely affecting the conveyed solid undesirably.

EXAMPLE

In the air oxidation of p-xylene in an acetic acid solution in the presence of heavy-metal and bromine ions conducted on a commercial scale, as disclosed in application Ser. No. 704,955 and British Pat. No. 1,237,786, the TPA is separated from the oxidation mixture by filtration or by centrifuging and the TPA is washed with acetic acid (HAc). The HAc-moist TPA is subsequently dried in a conventionally designed drier (flash drier, fluidized layer drier, belt drier, circulating drier). The TPA emerging from the drier is practically so dry that dust will not cling to it (residual moisture <0.1%), moreover, it has a temperature of from 90° to 100° C. (size of granules: 30 to 100μ).

This TPA is conveyed and metered into an esterification apparatus with a temperature of 320° to 330° C. under a guage pressure of 1 bar in accordance with U.S. Pat. Nos. 3,940,431; 3,972,912; 3,980,441 and 4,015,943 with the aid of an ES-pump.

The actual pump unit according to FIG. 1 consists of the rotor 1 made from high-grade steel which is driven by an electric motor having an infinitely variable speed control 2, and of the stator 3 made from an elastic material such as for example natural rubber, butyl rubber, NEOPRENE, HYPALON, VITON, soft-PVC, etc. The hot TPA entering from the storage container 4 into the receiving chamber of the pump 5 is fluidized with nitrogen to prevent bridge formation and solidifying. For this purpose, a nitrogen stream 6 is introduced by bubbling into the pump chamber 5 by way of the bottom sintered plate 7. The ES-pump is naturally aspirated and upon leaving the pump, the TPA conveyed in the direction from the suction side to the pressure side enters the transition section 8, which is flushed with a weak nitrogen stream 9. Thus when the TPA conveyance is interrupted, no 320° to 330° C. hot methanol vapor from the fluidized bed reactor 10 gets into the pump head and thereby damages the elastomer material of the stator, on the one hand, and thus, on the other hand, no TPA deposits appear in the intermediate section 8 during simultaneous moistening of the TPA by condensing methanol. As further protection for the temperature-sensitive stator from the high temperatures in the fluidized bed reactor 10 into which a 320° to 330° C. hot $CH_3OH$ vapor stream is introduced via a feed line 11, the intermediate section 8, located between the pump and the fluidization oven, can be cooled with water 12.

The conveyance stream of TPA, which is proportional to the speed, is completely free from pulsations. Thus an essential requirement for an optimal reaction of the pulverulent solid is fulfilled in the following apparatus, wherein in the selected example a constant esterification of the TPA is carried out with vaporous M. Even with the utilization of this pulverulent TPA, the otherwise usual aids such as nonreturn flaps, valves, priming the suction line, etc., are not needed. It is especially remarkable that no destruction of the elastic stator material takes place by friction and by localization of heat, although instead of the otherwise usual conveying liquid, a completely dry, pulverulent-crystalline product is transported between the stator and the rotor. Under the given conditions, even after an operating time of 1,000 or more hours, no destruction or severe wear and tear of the stator is observed and this happens, although the TPA coming from the drier of the oxidation stage has a temperature of approximately 100° C. and although the pump is directly connected to a 320° 330° C. hot system under superatmospheric pressure. The conveyance of TPA may be interrupted by turning off the pump; nevertheless, the sure pressure seal against the esterification system is maintained during shutdown time. The uniform mass stream is re-established instantly, i.e. without taking additional measures, by switching on the pump. Furthermore, it is valuable that those skilled in the art could also replace the stator in a short time, if required. With the incorporation of a valve, such as for example ball-valve 13, between the pump and fluidized bed reactor, this can also be successfully carried out during running operation, i.e. without switching off the supply of M and without the pressure release of the system.

We claim:

1. An eccentric screw pump for the metered conveying of pulverulent solids comprising:
    (a) a rotatable horizontal elongated pump shaft having a first end and a second end and means connecting said first end for rotation thereof;
    (b) a receiving chamber at said first end of said pump shaft;
    (c) a storage container open to atmospheric pressure above said receiving chamber for delivering said pulverulent solids;
    (d) a cylindrical pump chamber connected to said receiving chamber and surrounding said pump shaft at said second end;
    (e) an elastomer stator lining the inside of said cylindrical pump chamber and having a helical configuration with an elongated cross section and a double pitch;
    (f) a rotor on said pump shaft at said second end having a helical configuration with a circular cross section working in said stator;
    (g) an apparatus in which there is superatmospheric pressure of a gaseous system;
    (h) a transition section having means for cooling connecting said apparatus and said cylindrical pump chamber;
    (i) means for flushing said transition section with an inert gas; and
    (j) means for pneumatically loosening said pulverulent solids located in said receiving chamber comprising a bottom sintered metal plate and means for delivering an inert gas under pressure therethrough.

* * * * *